United States Patent [19]

Nimrod

[11] 4,274,408
[45] Jun. 23, 1981

[54] METHOD FOR GUIDE-WIRE PLACEMENT AND NOVEL SYRINGE THEREFOR

[76] Inventor: Beatrice Nimrod, 24 Wallace St., New Britain, Conn. 06051

[21] Appl. No.: 23,644

[22] Filed: Mar. 26, 1979

[51] Int. Cl.³ .............................................. A61M 5/00
[52] U.S. Cl. .................................................. 128/214.4
[58] Field of Search ............... 128/214 R, 214.4, 215, 128/220, 218 R, 218 P, 218 PA, 218 G, 218 M, 221, 234, 237, 348–349, DIG. 16, 9, 772

[56] References Cited

U.S. PATENT DOCUMENTS

| | | | |
|---|---|---|---|
| Re. 27,797 | 10/1973 | Sorenson | 128/214.4 |
| 1,950,137 | 3/1934 | Dowe | 128/220 |
| 3,013,559 | 12/1961 | Thomas | 128/340 |
| 3,097,646 | 7/1963 | Scislowicz | 128/214 |
| 3,220,411 | 11/1965 | Czorny | 128/214 |
| 3,370,587 | 2/1968 | Vizcarra | 128/214.4 |
| 3,527,216 | 9/1970 | Snyder | 128/220 |
| 3,547,103 | 12/1970 | Cook | 128/2.05 |
| 3,585,996 | 6/1971 | Reynolds | 128/214.4 |
| 3,685,513 | 8/1972 | Bellamy | 128/214.4 |
| 3,703,174 | 11/1972 | Smith | 128/214.4 |
| 3,792,703 | 2/1974 | Moorehead | 128/214.4 |
| 3,811,440 | 5/1974 | Moorehead | 128/214.4 |
| 3,825,001 | 7/1974 | Bennet et al. | 128/214.4 |
| 3,856,009 | 12/1974 | Winnie | 128/214.4 |
| 3,856,010 | 12/1974 | Moorehead | 128/214.4 |
| 3,877,429 | 4/1975 | Rasumoff | 128/214.4 |
| 3,903,885 | 9/1975 | Fuchs | 128/214.4 |
| 3,993,079 | 11/1976 | de Gatztanondo | 128/347 |
| 4,020,835 | 5/1977 | Nordstrom | 128/214.4 |
| 4,037,600 | 7/1977 | Poncy | 128/214.4 |

FOREIGN PATENT DOCUMENTS

2507119  9/1976  Fed. Rep. of Germany ........ 128/214.4

*Primary Examiner*—C. Fred Rosenbaum

[57] ABSTRACT

A syringe-type device for inserting a catheter guide wire into a blood vessel includes a syringe in which the plunger has a central passage extending through it. A thin feeder tube fits slidably in the central passage of the plunger and is itself provided with a central passage. The plunger passage is normally blocked by a closure means consisting of a ball bearing received in a seat provided by a rubber tip on inner edge of the plunger body. The needle is inserted into the blood vessel and the plunger is then withdrawn somewhat to permit blood to be observed in the body of the syringe for verification of proper needle positioning. The feeder tube is then slid through the central passage past the closure means to eject the ball bearing and thereby open the plunger passage. The feeder tube is further advanced to bring its inner end into contact with the end wall of the syringe body. In this position, the central passage of the feeder tube is aligned and in communication with the needle lumen, and the catheter guide wire may then be fed into the blood vessel by sliding it through the central passage of the feeder tube and the needle lumen. The device is then completely removed from the guide wire, and a beveled catheter is inserted over the guide wire in the usual manner.

11 Claims, 12 Drawing Figures

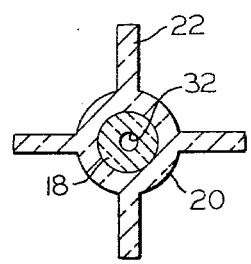
FIG. 4
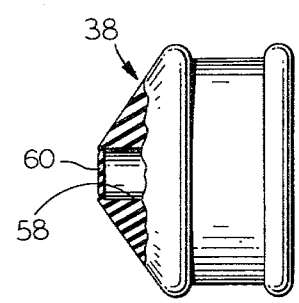
FIG. 12
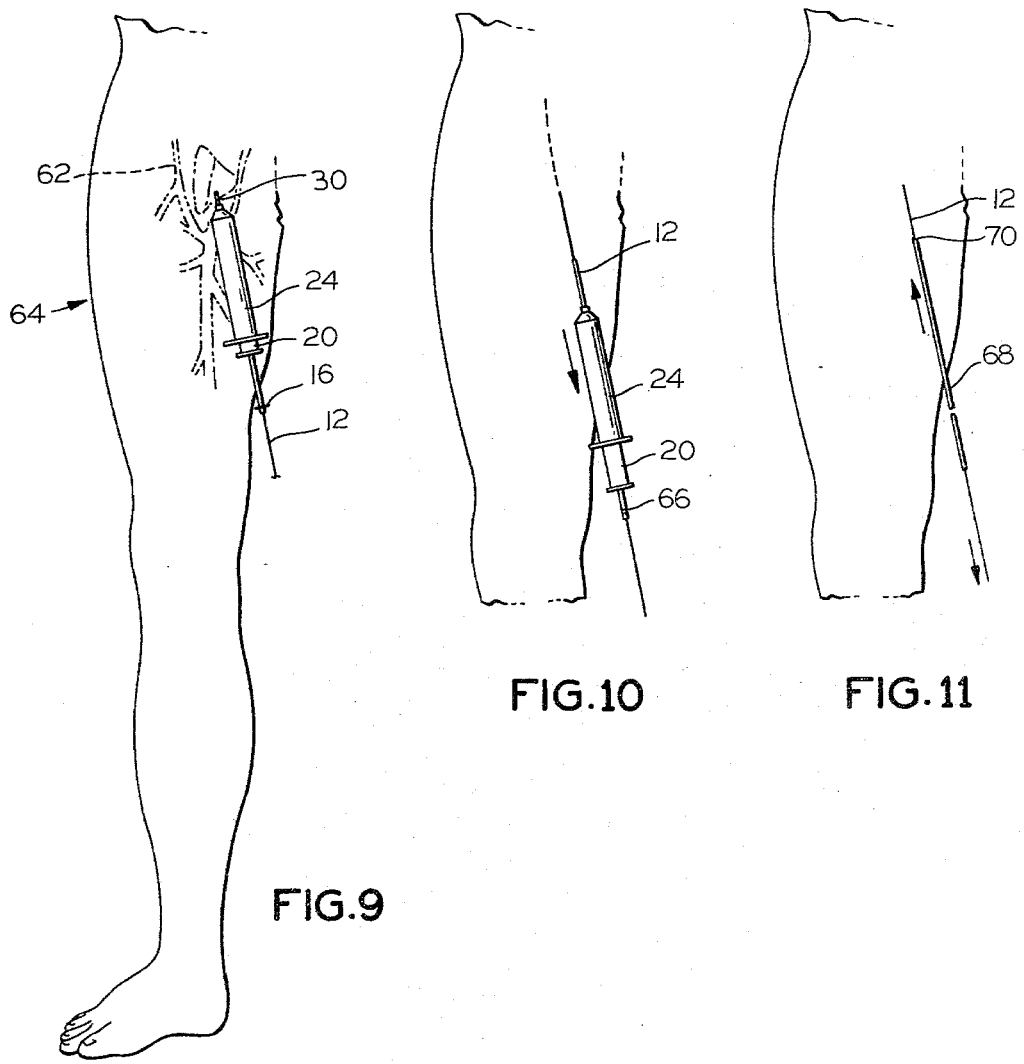
FIG. 9
FIG. 10
FIG. 11

METHOD FOR GUIDE-WIRE PLACEMENT AND NOVEL SYRINGE THEREFOR

BACKGROUND OF THE INVENTION

The present invention relates to the insertion of catheters into blood vessels.

It is common in the medical arts to insert catheters into blood vessels for various purposes such as pressure monitoring and parenteral infusion. As a result, a variety of techniques and devices for accomplishing the insertion are known. In one general method, catheters are inserted by the provision of a stiff needle that is located interior to and coaxial with the catheter and extends out its front end. The catheter is thereby inserted with the needle, and the needle may or may not be retracted following the insertion. Another general method employs a somewhat larger-diameter needle with the catheter carried inside.

The method and apparatus of the present invention are directed to still another general method, in which a guide wire is first inserted into the vein. The free end of the wire is threaded through the central passage of a catheter having a beveled forward edge, and the catheter is then inserted by being fed along the guide wire. This general method has numerous advantages, but part of the technique has been found both inconvenient for the medical personnel and unpleasant for the patient. It is necessary after the needle employed in this method has been inserted to retract it somewhat to determine that the intended blood vessel has been reached. This usually involves a fair amount of bleeding at the site of the insertion, which complicates the procedure for the doctor and can be disconcerting to the patient. Accordingly, it is an object of the present invention to test for proper positioning of the needle without the bleeding that has heretofore attended this technique.

SUMMARY OF THE INVENTION

The foregoing and related objects are achieved in a novel syringe device for inserting a catheter guide wire. The device includes a hollow body member providing a cavity therewithin and an end wall at one end thereof providing a hub portion and having an opening extending therethrough. A needle extends from the hub portion and has a needle lumen extending through it aligned with the opening in the end wall for communication of the lumen with the cavity. Extending through an opening in the opposite end of the body member is a plunger slidably received in the cavity, the peripheral surface of the plunger being in sliding and sealing engagement with a cooperating peripheral surface of the body member. The plunger has a plunger passage extending therethrough in alignment with the opening in the one end wall. A feeder tube is slidably received in the plunger passage, extends outwardly of the plunger, and has a feeder passage through it. The plunger passage is normally sealed on the needle side of said feeder tube by closure means, but the closure means permit the feeder tube to pass through it upon application of force to the feeder tube in the direction of the needle and thereby against the closure means. The inner end of the feeder tube is thereby slidable to a position adjacent the hub for communication of the feeder passage with the needle lumen to guide a catheter guide wire introduced through the outer end of the feeder tube into the needle lumen.

In the preferred embodiment, the closure means includes a seat portion that has a seat region of the plunger passage extending through it. The seat region of the plunger passage is bounded by an internal seat surface of the seat portion. The closure means further includes a substantially spherical member lodged in the seat region of the plunger passage, the seat portion of the plunger snugly holding the spherical member by sealing engagement of the seat surface therewith, but the closure means permits ejection of the spherical member from the passage by the sliding of the feeder tube through the seat portion of the plunger passage. The plunger can include a body member and a separate tip member on its inner end. The seat portion of the plunger includes the tip member in such an arrangement, and the tip member has the seat region of the plunger passage extending through it and providing the seat surface internally.

Alternately, the closure means can include a diaphragm extending across the plunger passage to seal it but permit the feeder tube to pass through it upon the application of force to the feeder tube in the direction of the needle and thereby against the diaphragm. The diaphragm can be slotted or frangible.

It is convenient for the feeder tube to have a slot extending into the passage and a generally U-shaped clip with one leg seated in the slot to extend transversely through the feeder passage. The clip is provided to restrain a guide wire contained in the feeder passage.

The method taught in this specification for inserting a catheter guide wire into a blood vessel includes inserting the needle of a syringe into the blood vessel and retracting the plunger to draw blood from the blood vessel through the lumen of the needle into the interior cavity of the syringe. This verifies proper positioning of the needle in the blood vessel. Without first removing the needle, the catheter guide wire is then fed through the syringe cavity and needle lumen into the blood vessel.

The step of feeding the catheter guide wire through the syringe cavity preferably includes feeding it from the outer end of the plunger through a plunger passage therethrough. The preferred method further includes, after the step of withdrawing blood and before the step of feeding the catheter guide wire, the step of sliding through the plunger passage an elongated feeder tube having a feeder passage therethrough. The feeder tube is slidably received in the plunger passage and extends outwardly of the plunger. In order to provide a guide path for the catheter guide wire, the feeder tube slides through a closure means normally sealing the plunger passage. The guide wire is fed through the feeder passage. If desirable, the plunger may be slid toward the needle after the step of retracting the needle to reinject the withdrawn blood into the blood vessel.

BRIEF DESCRIPTION OF THE DRAWINGS

These and further features and advantages of the present invention are described in connection with the attached drawings, in which:

FIG. 4 is a cross-sectional view of the plunger taken at line 4—4 of FIG. 3.

FIGS. 9, 10, and 11 are views illustrating the method of the present invention used to insert a catheter into a femoral artery; and FIG. 12 is a side view, partly in section, of a plunger tip of an alternate embodiment of the present invention.

DETAILED DESCRIPTION OF THE PREFERRED EMBODIMENT

Figure 1:
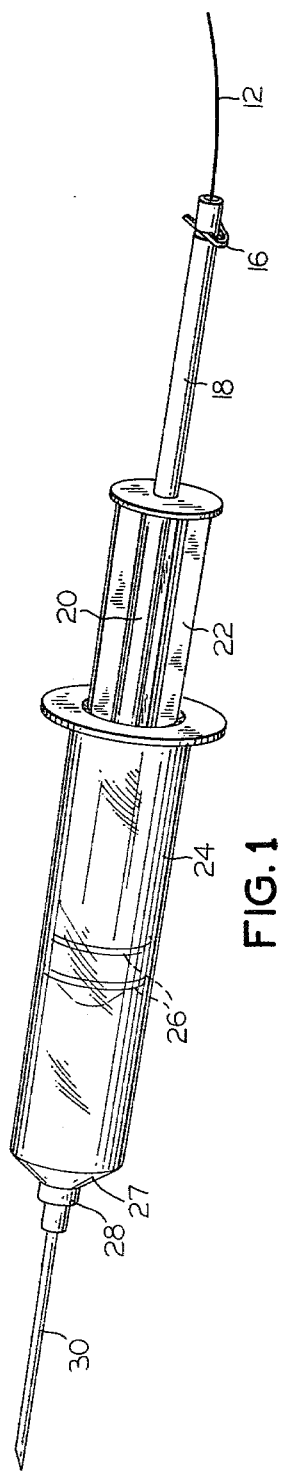
FIG. 1 is a perspective view of the syringe device of the present invention.

The apparatus of the present invention is exemplified by the embodiment of FIG. 1, which shows a syringe-type device with the customary body portion 24 terminating in an end wall 27 having a hub 28 disposed centrally thereof from which a needle 30 extends. A plunger 20 extends through an open end of the syringe body into its cylindrical interior cavity. The plunger is centered in the cavity by centering fins 20 and slidably mounted for longitudinal movement. Sealing surfaces 26 at one end of the plunger engage the peripheral walls so as to prevent fluid flow past surfaces 26. According to the present invention, a central passage through plunger 20 is provided to receive an elongated feeder tube 18 that itself has a central feeder passage through which to guide a catheter guide wire 12. A clip 16 is seated in a slot in the upper end of feeder tube 18. The clip holds catheter guide wire 12 in longitudinal position.

Figure 2:
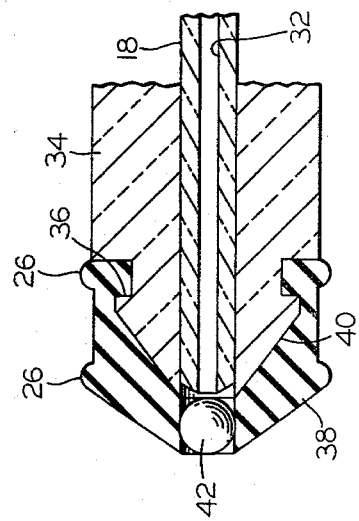
FIG. 2 is a sectional view of one end of the plunger of the device of the present invention.
Figure 3:
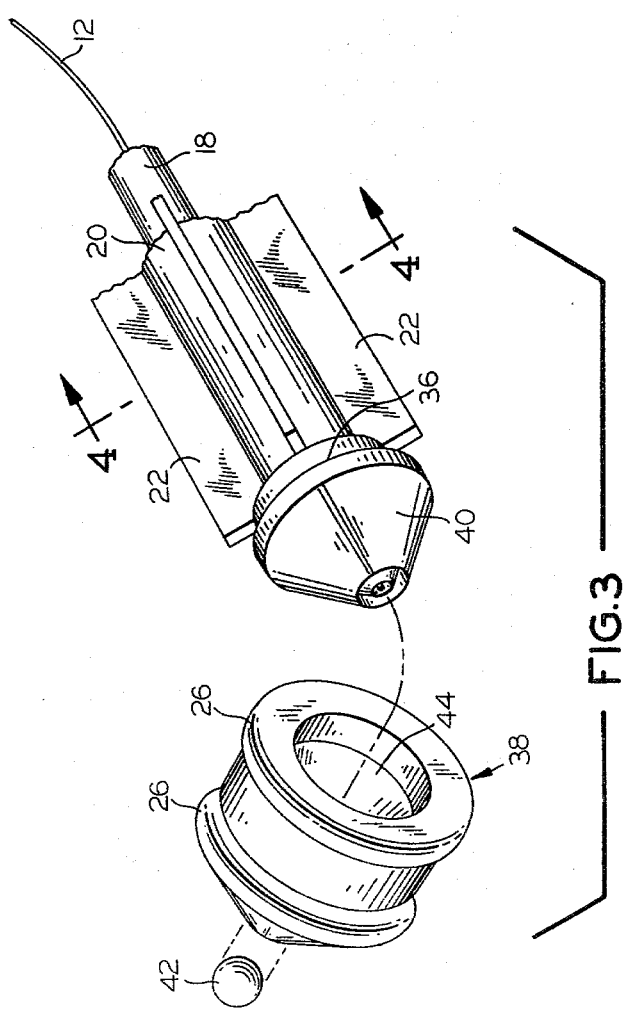
FIG. 3 is an exploded perspective view of the front end of the plunger with parts cut away.

The lower end of the plunger in the vicinity of the sealing surfaces 26 is shown in more detail in FIGS. 2, 3, and 4. As FIG. 2 shows, a body portion 34 of the plunger has a narrowed portion near the end and a clip 36 above a frustoconical portion 40. By means of lip 36, a rubber plunger tip with a cavity 44 in one end receives the frustoconical portion 40 of the plunger body in cavity 44. Feeder tube 18 is seen in a central passage of plunger 20, and the feeder passage 32 is shown to be coaxial with the plunger passage.

The resilient plunger tip 38 holds a ball bearing 42 in a seat region of the plunger passage. The peripheral wall of the seat region of the plunger passage acts as a seat that bears against ball bearing 42. Together, the plunger tip and the ball bearing act as closure means that prevent fluid flow from the lower end of the plunger into the plunger passage.

Figure 5:
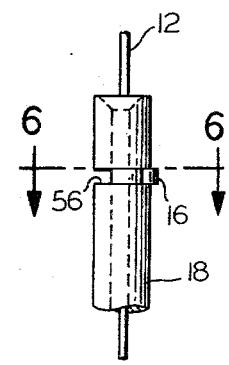
FIG. 5 is a vertical elevation of one end of the feeder tube of the present invention.

As FIG. 1 shows, a clip 16 is provided near the outer end of feeder tube 18. This is shown in more detail in FIGS. 5 and 6, where a slot is shown that provides a surface 56. Surface 56 is shown on end in FIG. 6, while the remainder of the feeder tube is shown in section. As can be appreciated from FIGS. 5 and 6, clip 16 is seated in the slot and extends transversely through the feeder passage 32 to hold guide wire 12 against the peripheral wall to inhibit its longitudinal movement. This has proved to be a convenient feature because a loose guide wire is rather annoying. Additionally, there is the possibility that without clip 16 the guide wire could slip out during the initial phase of the precedure.

Figure 7:
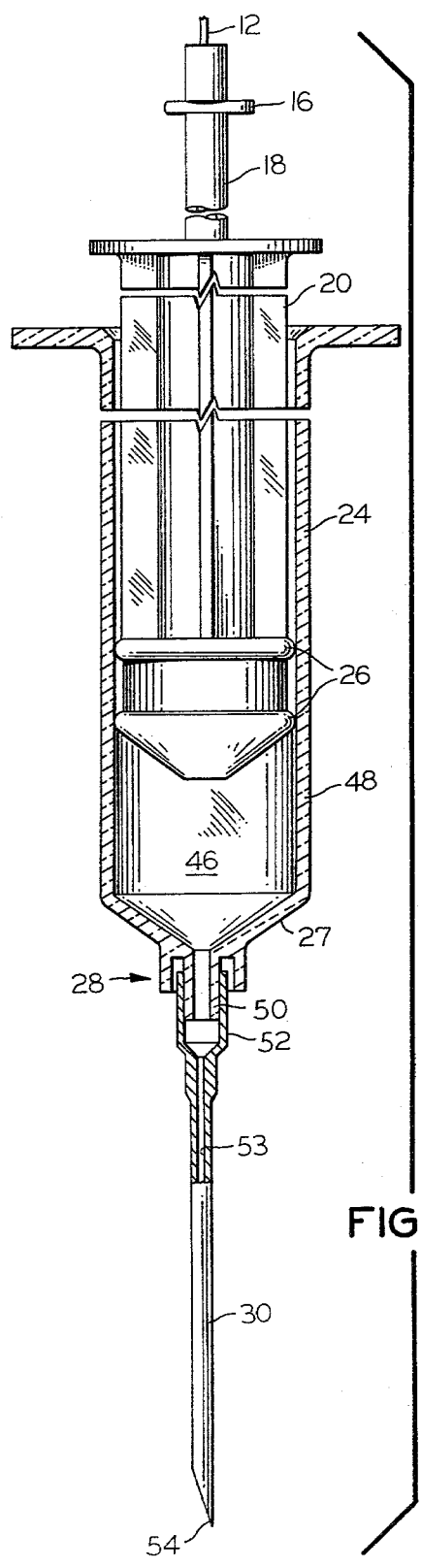
FIG. 7 is a vertical elevational view, partly in section, of the syringe device of the present invention.
Figure 7:
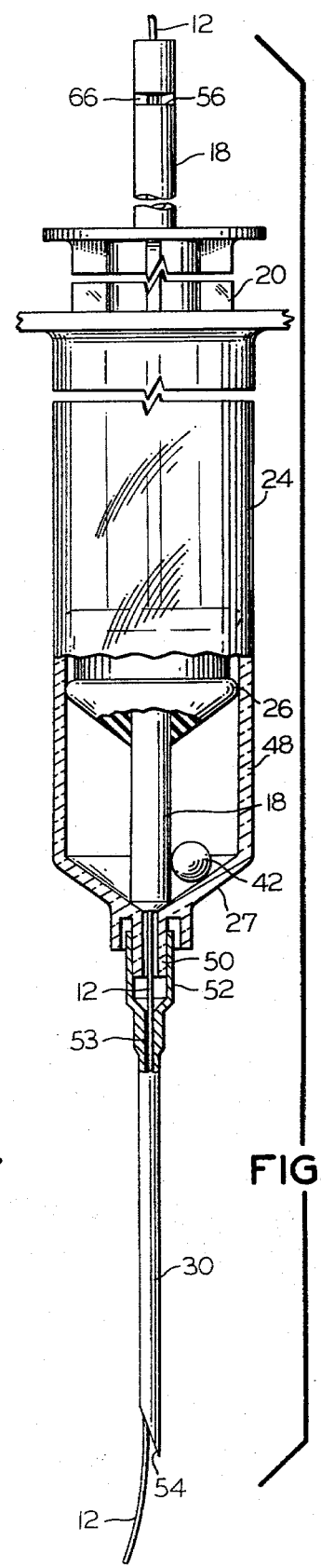
Figures 6, 8:
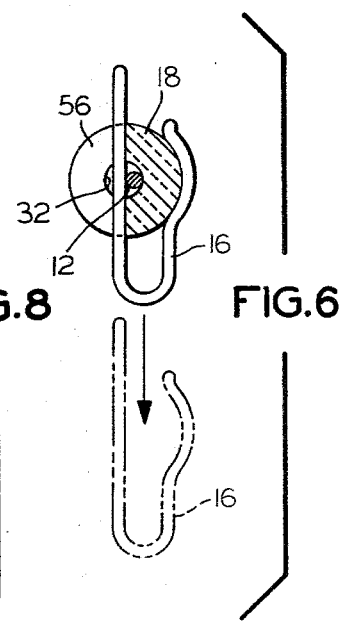
FIG. 6 is a cross-sectional view of the feeder tube taken at line 6—6 of FIG. 5.
FIG. 8 is a view similar to FIG. 7 with the feeder tube extending through the plunger-passage closure means.

FIGS. 7 and 8 show additional details of the syringe-like device of the present invention and illustrate its operation. The body member 24 of the syringe is shown with the plunger 20 extending into the interior cavity 46 of the syringe body. Peripheral sealing surfaces 26 on the plunger are shown sealing engaging the cooperating peripheral wall 48 of the syringe body. End wall 27 of the syringe body is seen in cross section providing a hub 28 from which an annular mounting post 50 extends to be received in an expanded upper end portion of needle 52. In the position shown in FIG. 7, feeder tube 18 has catheter guide wire 12 contained in it and held in place by clip 16. Feeder tube 18 is received in the plunger cavity with its upper end extending out through the upper end of plunger 20. Plunger 20 is shown as somewhat retracted in FIG. 7, a position to which it is moved after the sharpened tip 54 of needle 30 has been inserted into the blood vessel. Retraction of the plunger draws blood into interior cavity 46 so that the blood can be seen through transparent peripheral wall 48 to verify proper placement of the needle.

FIG. 8 shows a different position, in which feeder tube 18 has been advanced through the normal position of ball bearing 42. Application of force to feeder tube 18 slides it through the closure means that includes rubber tip 38 and ball bearing 40. This opens the closure means by pushing the ball bearing out of the way. Feeder tube 18 is further advanced to bring its inner end adjacent the end wall 27 at its hub 28. The clip 16 is then removed and the catheter guide wire 12 is fed through feeder tube 18 which guides it into needle lumen 53. Lumen 15 guides wire 12 into the blood vessel.

This operation can be understood more fully by considering FIGS. 7 and 8 in conjunction with FIGS. 9, 10, and 11. FIGS. 9, 10, and 11 show a leg 64 having an arterial system 62. The object of the technique in this case is to insert a catheter into a femoral artery. FIG. 9 shows the needle 30 having been inserted into the leg near the femoral artery with plunger 20 in the fully inserted position and feeder tube 18 in its normal, somewhat retracted position with clip 20 in place to hold catheter guide wire 12. In prior-art techniques the needle has typically been withdrawn at this point to verify proper positioning by observing the flow of blood from the blood vessel into which the needle has been inserted. According to the method of the present invention, however, the needle is not retracted at this point; instead, the plunger is retracted a short distance and proper positioning is verified by observation of blood flow into interior cavity 46 of syringe body 24. After proper positioning has been verified in this manner, the plunger may or may not be reinserted to return the blood, depending on the wishes of the medical personnel. In some cases the withdrawn blood can be used in tests, but it can be reinjected if it is not needed. It is assumed in the drawings that the plunger is not reinserted.

With the needle still in position in the blood vessel, feeder tube 18 is advanced down the plunger passage causing it to pass through the closure means and into contact with end wall 27 of the syringe body. This puts it into position to guide the catheter guide wire into needle lumen 53. With the device in this position shown in FIG. 8, the clip 16 is removed as previously indicated, and the catheter guide wire 12 is then fed through lumen 52 into the blood vessel.

With catheter guide wire 12 properly positioned in the blood vessel, the syringe device is retracted as suggested in FIG. 10. Since clip 16 has been removed, as indicated by reference numeral 66, the apparatus can be removed from the leg without removing catheter guide wire 12. The device is removed from both the leg and guide wire 12, leaving a free end of the guide wire 12 protruding from the leg.

The final step is shown in FIG. 11. A catheter 68 having a beveled front edge 70 is slipped over catheter guide wire 12 and inserted into the vein by being slid along guide wire 12. With catheter 68 in place, catheter guide wire 12 is withdrawn, thereby completing the procedure.

The preceding description will suggest many adaptations and variations to those skilled in the art. In particular, those skilled in the art will be aware of a number of other types of closure means. For instance, FIG. 12 illustrates a slightly different tip 38. This tip has the seat portion 58 of the plunger passage in it, but the passage is sealed by a diaphragm 60 instead of a ball bearing. Diaphragm 60 may be of the slotted variety known in the art, but it can also be a frangible diaphragm because the apparatus of the present invention will in many cases be used only once. It is thought that the ballbearing arrangement has some advantages because it permits a relatively even force to be applied to feeder tube 18 during the opening of the closure means, but the teachings of the present invention are clearly applicable to other types of closure means too.

It will be appreciated that the method and apparatus illustrated above enable the benefits of the guide-wire insertion method to be obtained without the unwelcome bleeding that had previously attended this method. Catheter insertion using the guide-wire method is thereby made easier for medical personnel; it is also thought that this type of procedure is somewhat less unpleasant for the patient.

Having thus described the invention, I claim:

1. A syringe device for inserting a catheter guide wire comprising:
   a. a hollow body member providing a cavity therewithin and an end wall at one end thereof providing a hub portion and having an opening extending therethrough;
   b. a needle on said hub portion and extending therefrom, said needle having a needle lumen extending therethrough and aligned with said opening in said end wall for communication of said lumen with said cavity;
   c. a plunger extending through an opening in the opposite end of said body member and slidably received in said cavity, the peripheral surface of said plunger being in sliding and sealing engagement with a cooperating peripheral surface of said body member, said plunger having a plunger passage extending therethrough in alignment with said opening in said one end wall;
   d. a feeder tube slidably received in said plunger passage, extending outwardly of said plunger, having inner and outer ends, and having a feeder passage extending from said outer end through said feeder tube to said inner end; and
   e. closure means normally sealing said plunger passage on the needle side of said feeder tube but permitting said feeder tube to pass therethrough upon application of force to said feeder tube in the direction of said needle, and thereby against said closure means, said inner end of said feeder tube thereby being slidable to a position adjacent said hub for communication of said feeder passage with said needle lumen to guide a catheter guide wire introduced through said outer end of said feeder tube into said needle lumen.

2. The syringe device of claim 1 wherein said closure means includes a diaphragm extending across said plunger passage to seal it but permitting the passage therethrough of said feeder tube upon the application of force to said feeder tube in the direction of said needle and thereby against said diaphragm.

3. The syringe device of claim 2 wherein said diaphragm is a slotted diaphragm.

4. The syringe device of claim 2 wherein said diaphragm is a frangible diaphragm.

5. A syringe device for inserting a catheter guide wire comprising:
   a. a hollow body member providing a cavity therewithin and an end wall at one end thereof providing a hub portion and having an opening extending therethrough, said body member also having an opening in the opposite end thereof providing communication with said cavity;
   b. a needle on said hub portion and extending therefrom, said needle having a needle lumen extending therethrough and aligned with said opening in said end wall for communication of said lumen with said cavity;
   c. a plunger extending through said opening in the opposite end of said body member and slidably received in said cavity, the peripheral surface of said plunger being in sliding and sealing engagement with a cooperating peripheral surface of said body member, said plunger having a plunger passage extending therethrough in alignment with said opening in said one end wall, said plunger including a seat portion of said plunger having a seat region of said plunger passage extending therethrough and bounded by an internal seat surface of said seat portion;
   d. a feeder tube slidably received in said plunger passage, extending outwardly of said plunger, and having a feeder passage therethrough; and
   e. substantially spherical member lodged in said seat region of said plunger passage, said seat portion of said plunger snugly holding said spherical member by sealing engagement of said seat surface therewith but permitting ejection thereof from said passage by the sliding of said feeder tube through said seat portion of said plunger passage, the inner end of said feeder tube thereby being slidable to a position adjacent said hub for communication of said feeder passage with said needle lumen to guide a catheter guide wire introduced through the outer end of said feeder tube into said needle lumen.

6. The syringe device of claim 5 wherein said plunger includes a body member and a separate tip member on the inner end thereof, said seat portion of said plunger including said tip member, said tip member having said seat region of said plunger passage extending therethrough and providing said seat surface internally thereof.

7. The syringe device of claim 6 or 5 wherein said feeder tube has a slot therein extending into said passage and a generally U-shaped clip with one leg thereof seated in said slot to extend through said feeder passage transversely thereof, said clip being adapted for restraining a guide wire contained in said feeder passage.

8. A syringe device for inserting a catheter guide wire comprising:

a. a hollow body member providing a cavity therewithin and an end wall at one end thereof providing a hub portion and having an opening extending therethrough, said body member also having an opening in the opposite end thereof providing communication with said cavity;

b. a needle on said hub portion and extending therefrom, said needle having a needle lumen extending therethrough and aligned with said opening in said end wall for communication of said lumen with said cavity;

c. a plunger extending through said opening in the opposite end of said body member and slidably received in said cavity, the peripheral surface of said plunger being in sliding and sealing engagement with a cooperating peripheral surface of said body member, said plunger having a plunger passage extending therethrough in alignment with said opening in said one end wall;

d. a feeder tube slidably received in said plunger passage, extending outwardly of said plunger, and having a feeder passage therethrough and a slot therein extending into said passage;

e. a generally U-shaped clip with one leg thereof seated in said slot in said feeder tube to extend through said feeder passage transversely thereof, said clip being adapted for restraining a guide wire contained in said feeder passage; and f. closure means normally sealing said plunger passage on the needle side of said feeder tube but permitting said feeder tube to pass therethrough upon application of force to said feeder tube in the direction of said needle, and thereby against said closure means, the inner end of said feeder tube thereby being slidable to a position adjacent said hub for communication of said feeder passage with said needle lumen to guide a catheter guide wire introduced through the outer end of said feeder tube into said needle lumen.

9. The syringe device of claim 8 wherein said closure means includes a diaphragm extending across said plunger passage to seal it but permitting the passage therethrough of said feeder tube upon the application of force to said feeder tube in the direction of said needle and thereby against said diaphragm.

10. The syringe device of claim 9 wherein said diaphragm is a slotted diaphragm.

11. The syringe device of claim 9 wherein said diaphragm is a frangible diaphragm.

* * * * *